April 4, 1961 M. L. MEILLAND Plant Pat. 2,040
ROSE PLANT
Filed June 27, 1960
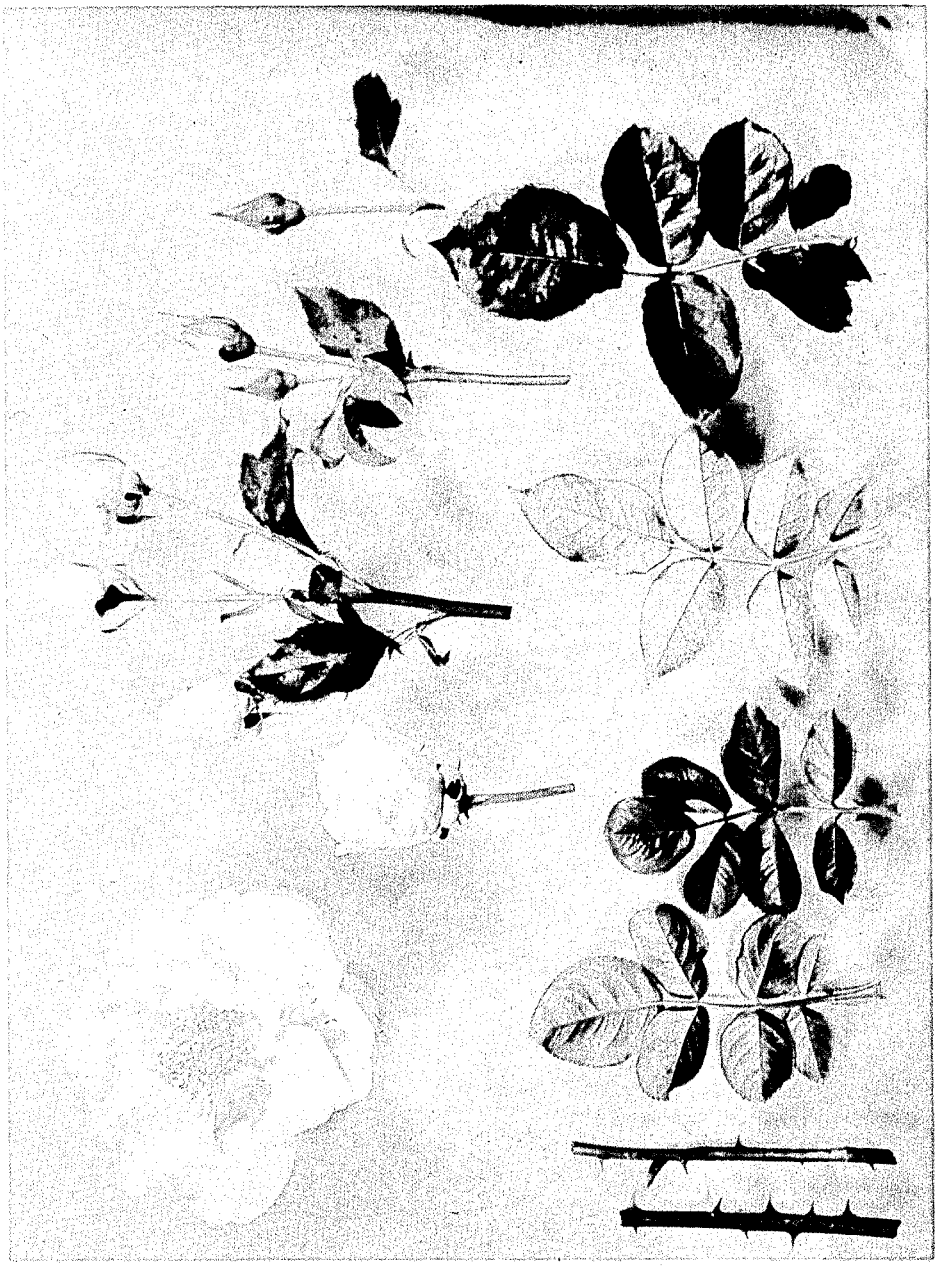
INVENTOR
Marie Louise Meilland
BY Robb & Robb
ATTORNEYS United States Patent Office Plant Pat. 2,040
Patented Apr. 4, 1961

2,040

ROSE PLANT

Marie Louise Meilland, Cap d'Antibes, Alpes Maritimes, France, assignor to The Conard-Pyle Company, West Grove, Pa., a corporation of Pennsylvania Filed June 27, 1960, Ser. No. 39,198

1 Claim. (Cl. 47—61)

The present invention relates to a new and distinct variety of rose plant of the hybrid polyantha class, which was originated by me by crossing the variety "Mme. Charles Sauvage" (unpatented) with the variety "Fashion" (U.S. Plant Patent No. 789).

The primary objective of this breeding was to produce a new rose variety in which there is combined all of the unusual qualities of the floribunda variety "Fashion" with the hybrid tea flower size of the variety "Mme. Charles Sauvage," but with different color tones in the flowers. This objective was fully achieved in the new variety which is the subject hereof, along with other improvements, as evidenced by the following unique combination of characteristics which are outstanding in the new variety and which distinguish it from its parents, as well as from all other varieties of which I am aware:

(1) Good vigor and plant habits;

(2) Excellent foliage which affords unusually good coverage of the plant and which has average resistance to all fungus diseases;

(3) An unusual floriferousness and continuity of bloom which is unique for a floribunda rose of large size;

(4) Semi-double flowers of large size, ranging from 3½ to 4 inches; and (5) A distinctive Barium Yellow general color tonality of the flowers which is maintained unusually evenly in the flowers from first opening to full bloom.

In comparison with its seed parent, "Mme. Charles Sauvage," the new variety is of the floribunda type instead of a hybrid tea like this parent; the flower size is somewhat smaller than that of this parent; and the flower color is a clear Barium Yellow instead of yellow tinted with saffron and with an orange center as in the flowers of this parent.

As compared with its pollen parent, "Fashion," the new variety has a plant habit which is more compact and the plants are more fully clothed with foliage; the flowers are much larger, thereby giving a fuller effect; and the flower color is Barium Yellow instead of the typical Coral Peach color of the flowers of this parent.

The flowers of my new variety are very similar in type to those of the variety of "Ivory Fashion" (U.S. Plant Patent No. 1,688), but the color of the flowers of the latter variety is Ivory White, whereas that of the new variety is Barium Yellow, and the new variety has a broader, more compact and more solid plant habit.

Asexual reproduction of the new variety by budding, as performed at West Grove, Pennsylvania, U.S.A., and also in France, shows that the foregoing characteristics and distinctions come true to form and are established and transmitted through succeeding propagations.

The accompanying drawing shows typical specimens of the vegetative growth and flowers of my new variety in different states of development and as depicted in color as nearly true as it is reasonably possible to make the same in a color illustration of this character.

The following is a detailed description of my new variety, with color terminology in accordance with the Horticultural Colour Chart of the Royal Horticultural Society, except where general color terms of ordinary dictionary significance are obvious:

Type: Hardy; bush; outdoor; seedling; for garden decoration.

Class: Hybrid polyantha (floribunda).

Breeding: Seedling.

*Seed parent.*—"Mme. Charles Sauvage."

*Pollen parent.*—"Fashion."

Propagation: Holds its distinguishing characteristics through succeeding propagations by budding.

*Flower*

Locality where grown and observed: West Grove, Pennsylvania, U.S.A.

Flowers borne: From 3 to 5 or more to stem; in regular rounded cluster; on stems of medium length and normal strength.

Quantity of bloom: Abundant, outdoors.

Continuity: Continuous.

Fragrance: Slight.

Bud:

*Peduncle.*—Short; slender; erect; stiff; rough; with numerous hairs of a color near Lettuce Green, Plate 861/2, with tips about Garnet Brown, Plate 00918/3. Color—near Lettuce Green, Plate 861/2, sometimes lightly overlaid with slightly lighter than Garnet Brown, Plate 00918/3.

*Before calyx breaks.* — Size — medium. Form — pointed-ovoid; with a conspicuous neck; usually without foliaceous appendages on the surface of the bud; with slender, entire foliaceous parts extending beyond the tip of the bud equal to ¼ of its length.

*As calyx breaks.*—Color—near Mimosa Yellow, Plate 602, sometimes shaded with Delft Rose, Plate 020/1.

*As first petal opens.*—Size—medium. Form—medium length; pointed. Color: outside—near Barium Yellow, Plate 503, sometimes washed with Delft Rose, Plate 020/1; inside—near Lemon Yellow, Plate 4/2, shading to Aureolin, Plate 3/1, at base.

*Opening.*—Opens up well.

Bloom:

*Size (when fully open).*—Large; from 3½ inches to 4 inches.

*Petalage.*—Double; from 20 to 25 petals; arranged regularly.

*Form.*—High-centered at first, but becoming cupped; petals being at first very loosely rolled inward but later becoming loosely rolled outward at maturity.

Petals: Medium thickness; soft; with both inside and outside satiny.

*Shape.*—Outer — obovate. Intermediate — obovate. Inner—undulate.

This description of a newly opened flower was made from a rose grown outdoors in the month of August at West Grove, Pennsylvania, U.S.A.:

*Color.*—Outer petal: outside surface—near Barium Yellow, Plate 503/2 at margin, bordering Barium Yellow, Plate 503; inside surface—near Primrose Yellow, Plate 601/3 at margin, bordering Barium Yellow, Plate 503, with point of attachment Aureolin, Plate 3/1. Intermediate petal: outside surface—Barium Yellow, Plate 503/1; inside surface—between Barium Yellow, Plate 503/1 and Barium Yellow, Plate 503/2, shading to Aureolin, Plate 3/1, at base and point of attachment. Inner petal: outside surface—Barium Yellow, Plate 503; inside surface—Barium Yellow, Plate 503, with point of attachment Aureolin, Plate 3/1.

This description was made from a rose that was open for three (3) days outdoors in the month of August at West Grove, Pennsylvania, U.S.A.:

*Color.*—Outer petal: outside surface—Barium Yellow, Plate 503/2, shading to Barium Yellow, Plate 503/1; inside surface—Primrose Yellow, Plate 601/3 over upper half of petal, shading to Barium Yellow, Plate 503/2 and then to Barium Yellow, Plate 503/1, with point of attachment Aureolin, Plate 3/1. Inner petal: outside surface—Barium Yellow, Plate 503/2; inside surface—Barium Yellow, Plate 503/2, with point of attachment Aureolin, Plate 3/1.

*General color effect.*—Newly opened flower—Barium Yellow, Plate 503/1. 3-days open—Barium Yellow, Plate 503/2.

*Behavior.*—Drop off cleanly.

*Flower longevity.*—On bush in garden—4 days in August.

*Reproductive organs*

Stamens: Many; arranged regularly about pistils.

Filaments: Most with anthers; from medium length to long. Color—Dresden Yellow, Plate 64/2.

Anthers: Medium size; all open at once; seldom an anther fused with a petaloid. Color—Lemon Yellow, Plate 4.

Pollen: Moderate abundance. Color—Aureolin, Plate 3.

Pistils: Medium number.

Styles: Uneven; from short to medium in length; medium heaviness; bunched.

Stigma: Color—Aureolin, Plate 3/2.

Ovaries: Some protruding from receptacle.

Hips: None observed.

Sepals: Permanent; medium length; spear-shaped.

Seeds: None observed.

*Plant*

Foliage:

*Leaves.*—Usually compound of 7, but sometimes only 5 or 3 leaflets; normal abundance; medium size; leathery.

*Leaflets.*—Shape—apex acute. Base—obtuse. Margin—simply serrate.

*Color.*—Mature: upper surface—near Spinach Green, Plate 0960; under surface—between nearly Lavender Green, Plate 000761/1 and Lavender Green, Plate 000761/2. Young: upper surface—near Spinach Green, Plate 0960/2, overlaid with Maroon, Plate 1030; under surface—near Pod Green, Plate 061, heavily overlaid with Erythrite Red, Plate 0027/1.

*Rachis (the supporting stem of the compound leaf).*—Medium caliper. Upper side—grooved; hairy. Under side—sparsely prickly.

*Stipules.*—Moderately long; narrow; with short points turning out at an angle of more than 45°.

*Disease resistance.*—Comparable to that of the average variety grown under the same cultural conditions at West Grove, Pennsylvania, U.S.A.

Growth:

*Habit.*—Bushy; much-branched.

*Growth.*—Vigorous.

*Canes.*—Medium caliper.

*Main stems.*—Dull. Color—Spinach Green, Plate 0960/2. Prickles—several; color—Fern Green, Plate 0862/3, overlaid with Garnet Brown, Plate 00918/3. Hairs—none.

*Branches.*—Dull. Color—Spinach Green, Plate 0960/2. Prickles—several; color—Fern Green, Plate 0862/3, overlaid with Garnet Brown, Plate 00918/3. Hairs—none.

*New shoots.*—Bright. Color—Lettuce Green, Plate 861/3. Prickles—several; color—near Garnet Brown, Plate 00918/3. Hairs—none.

I claim:

A new and distinct variety of rose plant of the hybrid polyantha (floribunda) class, substantially as herein shown and described, characterized particularly as to novelty by the unique combination of good vigor and plant habits, excellent foliage which affords unusually good coverage of the plant, with average resistance of said foliage to all fungus diseases, an unusual floriferousness and continuity of bloom, large size and semi-double form of the flowers, and a distinctive Barium Yellow general color tonality of the flowers which is maintained unusually evenly from first opening to full bloom.

No references cited.